United States Patent
Sasada et al.

(10) Patent No.: US 9,808,411 B2
(45) Date of Patent: Nov. 7, 2017

(54) LIP COSMETICS

(75) Inventors: Kaori Sasada, Yokohama (JP); Noriko Tomita, Yokohama (JP); Tomoko Ikeda, Yokohama (JP); Tomo Osawa, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/511,378

(22) PCT Filed: Sep. 16, 2010

(86) PCT No.: PCT/JP2010/066088
§ 371 (c)(1),
(2), (4) Date: May 23, 2012

(87) PCT Pub. No.: WO2011/065101
PCT Pub. Date: Jun. 3, 2011

(65) Prior Publication Data
US 2012/0237467 A1 Sep. 20, 2012

(30) Foreign Application Priority Data

Nov. 30, 2009 (JP) .................. 2009-272008
Dec. 11, 2009 (JP) .................. 2009-281965

(51) Int. Cl.
A61K 8/02 (2006.01)
A61K 8/81 (2006.01)
A61K 8/31 (2006.01)
A61K 8/58 (2006.01)
A61Q 1/04 (2006.01)
A61Q 1/06 (2006.01)

(52) U.S. Cl.
CPC .............. *A61K 8/8111* (2013.01); *A61K 8/31* (2013.01); *A61K 8/585* (2013.01); *A61Q 1/04* (2013.01); *A61Q 1/06* (2013.01)

(58) Field of Classification Search
CPC ........ A61K 8/31; A61K 8/585; A61K 8/8111; A61Q 1/06; A61Q 1/04
See application file for complete search history.

(56) References Cited

U.S. PATENT DOCUMENTS

| | | | |
|---|---|---|---|
| 5,672,339 A | 9/1997 | Soyama et al. | |
| 5,725,845 A | 3/1998 | Krog et al. | |
| 5,945,092 A | 8/1999 | Krog et al. | |
| 6,045,782 A | 4/2000 | Krog et al. | |
| 6,482,398 B1 | 11/2002 | Rabe et al. | |
| 2001/0031269 A1* | 10/2001 | Arnaud | .......... 424/401 |
| 2004/0151680 A1 | 8/2004 | Patil et al. | |
| 2004/0156806 A1* | 8/2004 | Patil | .......... A61Q 1/06 424/70.12 |
| 2004/0219122 A1 | 11/2004 | Masuda et al. | |
| 2005/0002724 A1 | 1/2005 | Blondeel et al. | |
| 2006/0228314 A1 | 10/2006 | Patil et al. | |
| 2007/0207103 A1 | 9/2007 | Masuda | |
| 2008/0057014 A1 | 3/2008 | Masuda et al. | |
| 2009/0010868 A1* | 1/2009 | Ilekti et al. | ............. 424/78.02 |
| 2012/0014895 A1 | 1/2012 | Ikeda et al. | |

FOREIGN PATENT DOCUMENTS

| | | |
|---|---|---|
| EP | 1661549 A1 | 5/2006 |
| EP | 2025321 A1 * | 2/2009 |
| JP | 9-48709 | 2/1997 |
| JP | 2000-053530 | 2/2000 |
| JP | 2001-199846 | 7/2001 |
| JP | 2004-168759 | 6/2004 |
| JP | 2005-501022 | 1/2005 |
| JP | 2005-343567 | 12/2005 |
| JP | 2006-282592 | 10/2006 |
| JP | 2007-238578 | 9/2007 |
| JP | 2007-277174 | 10/2007 |
| JP | 2008-133205 | 6/2008 |
| JP | 2009-529032 | 8/2009 |
| JP | 2010-090079 | 4/2010 |
| WO | 96/40044 | 12/1996 |
| WO | 97/16157 | 5/1997 |
| WO | 2004/071438 A2 | 8/2004 |
| WO | 2010/113956 | 10/2010 |

OTHER PUBLICATIONS

Patent Abstracts of Japan, Publication No. 2008-133205, Fourteen Pages.
Patent Abstracts of Japan, Publication No. 2004-168759, Twenty-Three Pages.
Patent Abstracts of Japan, Publication No. 2006-282592, Six Pages.
Patent Abstracts of Japan, Publication No. 2007-277174, Eight Pages.
Patent Abstracts of Japan, Publication No. 2007-238578, Thirteen Pages.
Patent Abstracts of Japan, Publication No. 2010-090079, Twelve Pages.

(Continued)

*Primary Examiner* — Robert Cabral
(74) *Attorney, Agent, or Firm* — Rankin, Hill & Clark LLP

(57) ABSTRACT

The present invention provides a lip cosmetic that has excellent secondary adhesion resistance effect immediately after the application and is excellent in gloss durability and stability. The lip cosmetic of the present invention is characterized by comprising the following components (a) to (d):

(a) 10 to 30 mass % of hydrogenated polyisobutene;
(b) 30 to 70 mass % of one or more kinds of methyl phenyl silicones that separate when mixed with (a) at 25° C.;
(c) 0.5 to 8 mass % of a lipophilic surfactant that does not separate both when mixed with component (a) and when mixed with component (b) at 90° C.; and
(d) 5 to 12 mass % of a wax.

14 Claims, 1 Drawing Sheet

(56) References Cited

OTHER PUBLICATIONS

Patent Abstracts of Japan, Publication No. 2000-053530, Ten Pages.
International Preliminary Report on Patentability, PCT/JP2010/066088, and Translation of Written Opinion, Six Pages.
European Search Report dated Sep. 11, 2013, Application No. 10832948.3, 8 pages.
English Abstract of JP 2005-343567 published Dec. 15, 2005, from Espacenet, 2 pages.
English Abstract of JP 2001-199846 published Jul. 24, 2001 from Espacenet, 2 pages.
English Abstract of JP 2005-501022 published Jan. 13, 2005 from Espacenet, 2 pages.

* cited by examiner

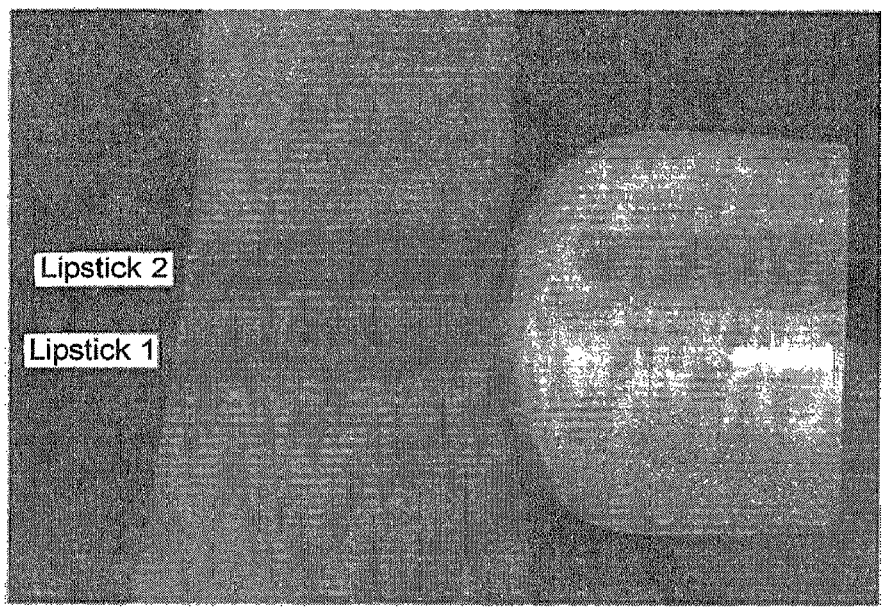

LIP COSMETICS

RELATED APPLICATIONS

This application claims the priority of Japanese Patent Application No. 2009-272008 filed on Nov. 30, 2009 and Japanese Patent Application No. 2009-281965 filed on Dec. 11, 2009, which are incorporated herein by reference.

FIELD OF THE INVENTION

The present invention relates to a lip cosmetic, and in particular, relates to a lip cosmetic having excellent secondary adhesion resistance effect immediately after the application and being excellent in gloss durability and stability.

BACKGROUND OF THE INVENTION

Conventional lip cosmetics have presented the problem of secondary adhesion, namely a lipstick is transferred onto a site contacted by a lip (for example, a cup) after the lipstick is applied to the lip. By contrast, lip cosmetics having so-called secondary adhesion resistance effect that causes little secondary adhesion have been developed.

For example, Patent Document 1 discloses a transfer-resistant cosmetic composition comprising: a volatile hydrocarbon solvent; a non-volatile silicone compound that can be dissolved or dispersed in the volatile hydrocarbon solvent; and non-volatile hydrocarbon oil that is dissolved in the volatile solvent and is incompatible with the non-volatile silicone compound, wherein the non-volatile hydrocarbon oil has a certain solubility parameter.

However, this transfer-resistant cosmetic composition has room for improvement in stability and gloss is insufficient. In addition, it takes some time until the onset of the secondary adhesion resistance effect after application. Since a volatile oil component is contained as an essential component, there is a problem in that some restrictions apply to the container.

Patent Document 2 discloses a lipstick composition having transfer resistance, comprising perfluoropolyether-type non-volatile oil and volatile oil, which are incompatible with each other. In this Patent Literature 2, oils are separated during application to a support to move onto a first composition.

However, the lipstick composition takes some time until the onset of the secondary adhesion resistance effect after application. Since a volatile oil component is contained as an essential component, there is a problem in that some restrictions apply to the container.

Patent Document 3 discloses a stick cosmetic having transfer resistance, comprising volatile oil and a silicone surfactant, wherein pigments are favorably dispersed.

However, this stick cosmetic has a large proportion of the volatile oil in the composition and thus has the disadvantage that its matte finish tends to provide a feeling of dryness on lips.

Patent Document 4 discloses a one-phase composition for lipsticks, comprising volatile oil and a silicone resin.

However, after evaporation of the volatile oil, this composition for lipsticks tends to cause a feeling of dryness over time, although it has improved transfer resistance. Moreover, a film of the resin remains on lips. The composition further has the following disadvantages that; it causes a filmy feeling and tightness, and the obtained adhesion is matte.

Patent Document 5 discloses an oil-in-oil emulsion composition comprising: continuous-phase oil comprising a silicone coating agent, volatile silicone oil, non-volatile silicone liquid oil, and an emulsifying agent; and dispersion-phase oil comprising ester oil and a coloring material, wherein the blending quantities of the continuous-phase oil and the dispersion-phase oil are at a dispersion-phase oil/(dispersion-phase oil and continuous-phase oil) ratio of 0.05 to 0.5.

However, it may be difficult to maintain for the oil-in-oil emulsion composition to maintain the temporal stability. In addition, it takes some time until the onset of the secondary adhesion resistance effect after application. Since a volatile oil component is contained as an essential component, there is a problem in that some restrictions apply to the container.

Patent literature 1: Japanese unexamined patent publication No. 2001-199846

Patent literature 2: International unexamined patent publication No. 96/40044

Patent literature 3: International unexamined patent publication No. 97/16157

Patent literature 4: Japanese unexamined patent publication No. H9-48709

Patent literature 5: Japanese unexamined patent publication No. 2000-53530

DISCLOSURE OF THE INVENTION

Problem to be Solved by the Invention

The present invention was made in view of the above-described conventional art. An object of the invention is to provide a lip cosmetic that has excellent secondary adhesion resistance effect immediately after the application and is excellent in gloss durability after application and stability.

Means to Solve the Problem

The present inventors have diligently studied; as a result, the present inventors have found that a lip cosmetic having a secondary adhesion resistance effect, without losing a gloss, from immediately after application can be obtained by using a specific oil component and by blending a specific lipophilic surfactant and wax.

That is, the lip cosmetic of the present invention is characterized by comprising the following components (a) to (d):

(a) 10 to 30 mass % of hydrogenated polyisobutene;
(b) 30 to 70 mass % of one or more kinds of methyl phenyl silicones that separate when mixed with (a) at 25° C.;
(c) 0.5 to 8 mass % of a lipophilic surfactant that does not separate both when mixed with component (a) and when mixed with component (b) at 90° C.; and
(d) 5 to 12 mass % of a wax.

In the lip cosmetic, it is preferable that a coloring material is contained.

In the lip cosmetic, it is preferable that a silicone-treated pearlescent agent is contained as the coloring material.

In the lip cosmetic, it is preferable that component (c) is one or more kinds selected from sorbitan sesquiisostearate, propylene glycol monostearate, cetyl PEG/PPG-10/1 dimethicone, and diglyceryl diisostearate.

In the lip cosmetic, it is preferable that the blending ratio (mass ratio) of component (a) and component (b) is component (b)/component (a)=1.1 to 6.

In the lip cosmetic, it is preferable that component (b) contains trimethyl pentaphenyl trisiloxane.

In the lip cosmetic, it is preferable that component (b) contains diphenylsiloxy phenyl trimethicone.

In the lip cosmetic, it is preferable that the blending quantity of diphenylsiloxy phenyl trimethicone is 1 to 17 mass % relative to the total amount of the cosmetic.

In the lip cosmetic, it is preferable that a volatile silicone oil and water and/or glycerin are contained.

In the lip cosmetic comprising diphenylsiloxy phenyl trimethicone, it is preferable that a volatile oil component isn't contained.

In addition, it is preferable that the lip cosmetic of the present invention comprises the following (a) to (d) and does not comprise a volatile oil component:
(a) 10 to 30 mass % of hydrogenated polyisobutene;
(b) 30 to 70 mass % of more than two kinds of methyl phenyl silicones that separate when mixed with (a) at 25° C. (however, it comprises 1 to 17 mass % of diphenylsiloxy phenyl trimethicone relative to the total amount of the cosmetic);
(c) 0.5 to 8 mass % of a lipophilic surfactant that does not separate both when mixed with component (a) and when mixed with component (b) at 90° C.; and
(d) 5 to 12 mass % of a wax.

In addition, it is preferable that the lip cosmetic of the present invention comprises the following components (a) to (d), 3 to 15 mass % of a volatile silicone oil, and 3 to 12 mass % of water and/or glycerin:
(a) 10 to 25 mass % of hydrogenated polyisobutene;
(b) 30 to 65 mass % of one or more kinds of methyl phenyl silicones that separate when mixed with (a) at 25° C.;
(c) 2 to 7 mass % of diglyceryl diisostearate; and
(d) 5 to 12 mass % of a wax.

Effect of the Invention

A lip cosmetic having secondary adhesion resistance from immediately after the application, gloss durability, and good stability, can be obtained by blending the specific amounts of (a) hydrogenated polyisobutene, (b) one or more kinds of methyl phenyl silicones that separate when mixed with (a) at 25° C., (c) a lipophilic surfactant that does not separate both when mixed with component (a) and when mixed with component (b) at 90° C., and (d) a wax.

BRIEF DESCRIPTION OF THE DRAWINGS

FIG. 1 shows the secondary adhesion resistance effect of the lip cosmetic of the present invention.

BEST MODE FOR CARRYING OUT THE INVENTION

In the present invention, by blending hydrogenated polyisobutene and methyl phenyl silicone(s) that are not compatible therewith, an oil-in-oil cosmetic, wherein methyl phenyl silicone(s) form a continuous phase, the coloring material and hydrogenated polyisobutene form a dispersed phase, and a lipophilic surfactant is present at the interface, is prepared. Because the silicone oil separates into the surface layer on the lip upon application, a gloss is provided. And the hydrogenated polyisobutene in the inner layer holds in the coloring material. On this occasion, the silicone oil separates into the surface layer upon application because the viscosity difference between the continuous phase and the dispersed phase is large; thus the secondary adhesion resistance effect is instantaneously attained.

In the following, each component is described in detail.

((a) Hydrogenated Polyisobutene)

(a) hydrogenated polyisobutene used in the present invention is the oil component which adheres on the lip and is insoluble in component (b) which is continuous phase oil component. It is preferable that the average molecular weight of the hydrogenated polyisobutene is 1000 to 2650.

It is necessary that the blending quantity of (a) hydrogenated polyisobutene is 10 to 30 mass % relative to the total amount of the cosmetic. The blending quantity is preferably 12 to 25 mass % and especial preferably 12 to 20 mass %. If the blending quantity is too large, the secondary adhesion resistance effect isn't attained because it is difficult for the cosmetic to separate upon application. If it is too small, the secondary adhesion resistance effect isn't be attained because the cosmetic isn't separated upon application.

Hydrogenated polyisobutene and the continuous phase oil component are poorly miscible. Therefore, even when other nonvolatile oil components are mixed, a phase separation state can be maintained in the used temperature range so far as the quantity is within a certain range. Accordingly, nonvolatile oil components compatible with hydrogenated polyisobutene can be blended in the range that a phase separation state can be maintained and in the range that the secondary adhesion resistance effect is not impaired. Oil components generally used in lip cosmetic can be used as such oil components. The examples of such oil components include liquid paraffin, squalane, glyceryl diisostearate trimethylol propane tri-2-ethyl isostearate, isopropyl myristate, cetyl-2-ethyl hexanoate, glyceryl triisostearate, 2-heptyl undecyl palmitate, methyl polysiloxane, glyceryl triisostearate, and diisostearyl malate. One or more such any oils can be selected.

((b) Methyl Phenyl Silicone)

(b) methyl phenyl silicone used in the present invention separates when mixed with (a) hydrogenated polyisobutene at 25° C. When the lip cosmetic of the present invention, wherein such component (b) is used, is applied on the lip, component (a) and component (b) instantaneously separate upon the contact of the lip cosmetic and the lip. As a result, component (a) adheres on the lip, and component (b) separates into the surface layer; thus the secondary adhesion resistance effect is attained. When such a lip cosmetic sticks to a material, only transparent component (b) sticks to the material. In addition, because a large amount of component (b) is present, component (b) again separates into the surface layer after the contact of the material and the lip. Therefore the lip cosmetic of the present invention can attain the secondary adhesion resistance effect for a long time.

The (b) methyl phenyl silicone blended in the lip cosmetic of the present invention can be one kind or a mixture of two or more kinds.

Here, the presence or absence of "separation" was measured under the following conditions.

(Measurement Condition)

(a) and (b) were used in the ratio ((a):(b)=1:3 (mass ratio)) and heated to 90° C. After the mixture was mixed with stirring, it was allowed to stand at 25° C. When the boundary was uniformly separated into two layers, it was denoted "separated". When it was a translucent state or a transparently miscible state without a boundary, it was denoted "not separated".

Trimethyl pentaphenyl trisiloxane is preferable as (b) methyl phenyl silicone blended in the lip cosmetic of the present invention. It is especially preferable that 50 mass % or more of trimethyl pentaphenyl trisiloxane is contained relative to the total amount of (b) methyl phenyl silicones.

Examples of trimethyl pentaphenyl trisiloxanes include methyl phenyl silicone FZ3156 (165 mm$^2$/s (25° C.), manufactured by Dow Corning Toray Co., Ltd.).

Diphenylsiloxy phenyl trimethicone is also preferable as (b) methyl phenyl silicone blended in the lip cosmetic of the present invention. By blending diphenylsiloxy phenyl trimethicone, the gloss upon application is more improved. As the diphenylsiloxy phenyl trimethicone, it is especially preferable that it having 10 to 25 mm$^2$/s (25° C.) of viscosity is used. Examples of diphenylsiloxy phenyl trimethicones include silicone KF56 (14 mm$^2$/s (25° C.), manufactured by Shin-Etsu Chemical Co., Ltd.)).

The blending quantity of diphenylsiloxy phenyl trimethicone is preferably 1 to 17 mass % relative to the total amount of the cosmetic and especial preferably 5 to 10 mass %. If the blending quantity of diphenylsiloxy phenyl trimethicone is less than 1 mass %, the cosmetic may be separated because the compatibility of the bulk material may be poor. If it exceeds 17 mass %, the secondary adhesion resistance effect may not be attained because the cosmetic may not be separated upon application.

As components (b) blended in the lip cosmetic of the present invention, as well as the above components, diphenyl dimethicone (for example, silicone KF54 (400 mm$^2$/s (25° C.), manufactured by Shin-Etsu Chemical Co., Ltd.), silicone KF50-300CS (270 to 330 mm$^2$/s (25° C.), manufactured by Shin-Etsu Chemical Co., Ltd.), silicone KF-54HV (5000 mm$^2$/s (25° C.), manufactured by Shin-Etsu Chemical Co., Ltd.)), phenyl trimethicone (for example, silicone SH556 (22 mm$^2$/s (25° C.), manufactured by Dow Corning Toray Co., Ltd.)), and the like can be used.

The blending quantity of component (b) is 30 to 70 mass % relative to the total amount of the cosmetic and preferably 40 to 60 mass %. If the blending quantity of component (b) is less than 30 mass %, the secondary adhesion resistance effect isn't attained because it is difficult for the cosmetic to separate upon application. If it exceeds 70 mass %, the secondary adhesion resistance effect isn't attained because the blending quantity of hydrogenated polyisobutene decreases.

In the present invention, it is preferable that the blending ratio (mass ratio) of component (a) and component (b) is component (b)/component (a)=1.1 to 6. If component (b)/component (a) is less than 1.1, the secondary adhesion resistance effect may not be attained because it may be difficult for the cosmetic to separate upon application. If it exceeds 6, the secondary adhesion resistance effect may not be attained because the blending quantity of hydrogenated polyisobutene may be too small.

((c) Lipophilic Surfactant)

It is necessary that the lipophilic surfactant used in the present invention does not separate both when mixed with component (a) and when mixed with component (b) at 90° C. By blending such a lipophilic surfactant, a stable lip cosmetic wherein non-compatible component (a) and component (b) are blended can be produced.

Here, the presence or absence of "separation" was measured under the following conditions.

(Measurement Condition)

(c) and (a) were used in the ratio ((c):(a)=1:1 (mass ratio)) and heated to 90° C. and mixed with stirring. When the boundary was uniformly separated into two layers, it was denoted "separated". When it was a translucent state or a transparently miscible state without a boundary, it was denoted "not separated".

The relationship with (b) is also the same as above.

The lipophilic surfactant blended in the present invention can be one kind or a mixture of two or more kinds.

It is especially preferable that the lipophilic surfactant does not separate when mixed with (a) at 25° C. and separates when mixed with (b) at 25° C.

Sorbitan sesquiisostearate, propylene glycol monostearate, cetyl PEG/PPG-10/1 dimethicone, and diglyceryl diisostearate are preferable as (c) lipophilic surfactant blended in the lip cosmetic of the present invention.

As a commercial sorbitan sesquiisostearate, ESTEMOL 182V (manufactured by The Nisshin OilliO Group, Ltd.) can be listed. As a commercial propylene glycol monostearate, Nikkol PMS-SEN (manufactured by Nikko Chemicals Co., Ltd.) can be listed. As a commercial cetyl PEG/PPG-10/1 dimethicone, ABIL EM90 (manufactured by Evonik Degussa Japan Co., Ltd.) can be listed. As a commercial diglyceryl diisostearate, WOGEL-18DV (manufactured by MATSUMOTO TRADING Co., Ltd.) can be listed.

The blending quantity of component (c) is 0.5 to 8 mass % relative to the total amount of the cosmetic and preferably 1 to 5 mass %. If the blending quantity of component (c) is less than 0.5 mass %, the compatibility of the bulk material is poor, thus the cosmetic is separated. If it exceeds 8 mass %, the secondary adhesion resistance effect isn't attained because the cosmetic isn't separated upon application.

When the allowable blending quantities of the respective components (a) to (c) are heated to 90° C. and mixed with stirring, a translucent state or a transparently miscible state without a boundary, namely the above-described "not separated" state is preferably formed.

((d) Wax)

(d) wax blended in the lip cosmetic of the present invention is not limited in particular as long as it can be normally blended for cosmetics.

In the present invention, an oil-in-oil solid lip cosmetic, wherein (b) methyl phenyl silicone that is a liquid oil component and normally has lower viscosity than component (a) is the external phase, can be obtained by blending (d) wax. That is, it is preferable that the wax used in the present invention is compatible with the methyl phenyl silicone.

Examples of the waxes used in the present invention include carnauba wax, candelilla wax, polyethylene wax, beeswax, ceresin, microcrystalline wax, solid paraffin, and Japan wax. In the waxes, microcrystalline wax and polyethylene wax are preferable.

The blending quantity of component (d) is 5 to 12 mass % relative to the total amount of the cosmetic and preferably 6 to 11 mass %. If the blending quantity of component (d) is less than 5 mass %, the solidification is difficult. If it exceeds 12 mass %, the spreadability becomes heavy and the gloss is lost.

In the present invention, it is preferable to blend a coloring material in addition to the above-described essential components (a) to (d). Examples of the coloring material include those normally used in lip cosmetics.

Such coloring materials can be powdery or lake-like (oil-containing state) so far as they are coloring materials normally used in lipsticks. They can be inorganic pigments, organic pigments, or pearlescent agents. Inorganic pigments, organic pigments, and pearlescent agents are all more wettable to the dispersed-phase oil component (component (a)) than to the continuous phase oil component (component (b)). Accordingly, the coloring material spontaneously moves into the dispersed-phase oil component. Therefore, the coloring material is held in (a) hydrogenated polyisobutene when the cosmetic is applied and it is present in the inner side of component (b) of surface layer; thus the secondary adhesion is difficult to take place.

In the case that a pearlescent agent is blended as the coloring material, it is preferable that a silicone-treated pearlescent agent is blended. Since the silicone-treated pearlescent agent is used, the coloring material can be easily dispersible during production.

When a silicone-treated pearlescent agent is used, it is wettable to the continuous phase oil component (component (b)). However, when the cosmetic is applied, a pearlescent agent moves into component (a) because the pearlescent agent has a high aspect ratio normally. Therefore even in the case that the silicone-treated pearlescent agent is blended in the cosmetic of the present invention, the secondary adhesion resistance effect is excellent.

The blending quantity of coloring material is preferably 3 to 15 mass % relative to the total amount of the cosmetic and especial preferably 5 to 10 mass %. If the blending quantity of coloring material is too small, the secondary adhesion resistance effect may be difficult to be felt.

The blending quantity of pearlescent agent is preferably less than 5 mass %. If it is too large, the spreadability may be poor.

In the lip cosmetic of the present invention, in addition to the above-described components, the components normally used in lip cosmetics (for example, oil other than the above-described oils, powder, polymer compound, moisturizer, perfume, antioxidant agent, preservative, and beauty component) can be blended so far as the effect of the present invention is not undermined.

The examples of moisturizers include polyol moisturizers such as propylene glycol and 1,3-butylene glycol.

In the present invention, the stability is improved by blending a volatile silicone oil and water and/or glycerin.

As such volatile silicone oil, it is not limited to, but decamethylcyclopentasiloxane is preferable. The blending quantity of the volatile silicone oil is preferably 3 to 15 mass % relative to the total amount of the cosmetic. If the blending quantity of the volatile silicone oil is too small, the stability may be poor. If it is too large, the moistness may be lost.

The blending quantity of water and/or glycerin is preferably 3 to 12 mass % relative to the total amount of the cosmetic and especial preferably 5 to 9 mass %. If the blending quantity of water and/or glycerin is too small, the stability may be poor. If it is too large, the dispersibility of the coloring agent may be poor. Of these components, only glycerin may be blended without water. That is, the content of glycerin is preferably 25 to 100 mass %, and more preferably 25 to 75 mass % in water and/or glycerin.

However, in the present invention, in the case that diphenylsiloxy phenyl trimethicone is blended as (b) methyl phenyl silicone, it is preferable that the volatile oils, water, and glycerin are not blended. Here, "not blended" means that nothing is blended except for unintentional contaminants such as impurities.

That is, when diphenylsiloxy phenyl trimethicone is blended, a lip cosmetic with excellent stability can be obtained without blending a volatile oil component, water, and glycerin. In the case of such a lip cosmetic, the accommodation in an air-tight container (container that can prevent the evaporation of a volatile component) is not necessary; thus there is a merit in that there is no container restriction.

It is preferable that the lip cosmetic of the present invention is constituted so that the separation does not take place throughout the entire production process and the state of one homogeneous phase is maintained.

The lip cosmetic of the present invention can be applied to lipsticks, lip glosses, lip bases, overcoats for lipsticks, lip creams, and the like. In particular, a solid lipstick is preferable.

EXAMPLES

The present invention will be further described in the following examples. However, the invention is not limited by these examples. Unless otherwise specified, the blending quantity of each component will be expressed in mass %.

Prior to illustrating the examples, the methods for the evaluation tests used in the present invention will be explained.

Evaluation (1): Evaluation Test of the Secondary Adhesion Resistance Effect

The actual usability test by 10 professional panelists was carried out. The five-level sensory evaluation (scoring) of the secondary adhesion resistance effect upon application to the lip was based on the below-described scoring criteria. The determination was by the score average value based on the below-described evaluation criteria.

(Score)
5 points: very excellent
4 points: excellent
3 points: ordinary
2 points: poor
1 point: very poor
(Evaluation Criteria)
S: The score average value is 4.5 point or higher and less than 5 points.
A*: The score average value is 4 point or higher and less than 4.5 points.
A: The score average value is 3.3 point or higher and less than 4 points.
B: The score average value is 2.5 point or higher and less than 3.3 points.
C: The score average value is 1 point or higher and less than 2.5 points.

The examples listed with "-" in the table had poor stability, and the secondary adhesion resistance effect could not be measured.

Evaluation (2): Evaluation Test of the Stability of the Sample (Bulk Material)

The stability of the material obtained by allowing 100 g of the sample, which was prepared by heating to 90° C. and mixing, to be cooled at room temperature (25° C.) was evaluated based on the following evaluation criteria.

(Evaluation Criteria)
A: uniform and not separated
C: non-uniform and separated

Evaluation (3): Evaluation Test of the Stability of the Sample (after Molding)

The wax uniformity of the cutting plane of the stick-shaped sample was evaluated based on the below-described evaluation criteria.

(Evaluation Criteria)
A*: uniform
A: slightly uniform
B: slightly non-uniform
C: non-uniform Evaluation (4): Evaluation Test of the Appearance of the Sample (Bulk Material)

The appearance of the material obtained by allowing 100 g of the sample, which was prepared by heating to 90° C. and mixing, to be cooled at room temperature (25° C.) was evaluated based on the following evaluation criteria.

(Evaluation Criteria)
A: There is no aggregation of coloring material, and it is uniform.
B*: There is an slight aggregation of coloring material.
B: There is an aggregation of coloring material
C: There is an abundant aggregation of coloring material, and it is non-uniform.

Evaluation (5): Evaluation Test of the Spreadability

The actual usability test by 10 professional panelists was carried out. The five-level sensory evaluation (scoring) of the spreadability upon application to the lip was based on the below-described scoring criteria. The determination was by the score average value based on the below-described evaluation criteria.

(Score)
5 points: very excellent
4 points: excellent
3 points: ordinary
2 points: poor
1 point: very poor (Evaluation Criteria)
S: The score average value is 4.5 point or higher and less than 5 points.
A*: The score average value is 4 point or higher and less than 4.5 points.
A: The score average value is 3.3 point or higher and less than 4 points.
B: The score average value is 2.5 point or higher and less than 3.3 points.
C: The score average value is 1 point or higher and less than 2.5 points.

At first, samples (solid lipsticks) with the blending compositions shown in the below Tables 1 and 2 were produced by the ordinary method. Respective samples were evaluated, for the evaluation items (1) and (2), based on the above rating criteria. The result is shown in Tables 1 and 2.

All the methyl phenyl silicones used in the following Examples and Comparative Examples were those that separate when mixed with hydrogenated polyisobutene at 25° C.

TABLE 1

|  | Comparative Example 1 | Example 1 | Example 2 | Example 3 | Example 4 | Example 5 | Example 6 |
| --- | --- | --- | --- | --- | --- | --- | --- |
| Hydrogenated polyisobutene·X·1 | 19 | 15 | 15 | 15 | 15 | 15 | 10 |
| Diphenyl dimethicone·X·2 | 14 | 14 | 14 | 14 | 14 | 10 | 10 |
| Trimethyl pentaphenyl trisiloxane·X·3 | 40 | 40 | 40 | 40 | 40 | 40 | 40 |
| Diphenylsiloxy phenyl trimethicone·X·4 | 9 | 9 | 9 | 9 | 9 | 15 | 15 |
| Mineral oil | — | — | — | — | — | — | 5 |
| Sorbitan sesquiisostearate·X·5 | — | 4 | — | — | — | 2 | 2 |
| Diglyceryl diisostearate·X·6 | — | — | 4 | — | — | — | — |
| Cetyl PEG/PPG-10/1 dimethicone·X·7 | — | — | — | 4 | — | — | — |
| Propylene glycol monostearate·X·8 | — | — | — | — | 4 | — | — |
| Polyethylene wax | 7 | 7 | 7 | 7 | 7 | 7 | 7 |
| Coloring material, pearlescent agent | 11 | 11 | 11 | 11 | 11 | 11 | 11 |
| Evaluation (1): Secondary adhesion resistance effect | A* | A* | A* | A* | A* | A* | A* |
| Evaluation (2): Stability of the sample (bulk material) | C | A | A | A | A | A | A |

TABLE 2

|  | Comparative Example 2 | Comparative Example 3 | Comparative Example 4 | Comparative Example 5 | Comparative Example 6 | Comparative Example 7 | Comparative Example 8 | Comparative Example 9 |
| --- | --- | --- | --- | --- | --- | --- | --- | --- |
| Hydrogenated polyisobutene·X·1 | 15 | 15 | 15 | 15 | 15 | 15 | 15 | 15 |
| Diphenyl dimethicone·X·2 | 14 | 14 | 14 | 14 | 14 | 14 | 14 | 14 |
| Trimethyl pentaphenyl trisiloxane·X·3 | 40 | 40 | 40 | 40 | 40 | 40 | 40 | 40 |
| Diphenylsiloxy phenyl trimethicone·X·4 | 9 | 9 | 9 | 9 | 9 | 9 | 9 | 9 |
| Lauryl PEG-9 polydimethylsiloxyethyl dimethicone·X·9 | 4 | — | — | — | — | — | — | — |
| Glyceryl behenate/eicosadioate·X·10 | — | 4 | — | — | — | — | — | — |
| Sorbitan laurate | — | — | 4 | — | — | — | — | — |
| Sorbitan isostearate | — | — | — | 4 | — | — | — | — |
| PEG-10 hydrogenated castor oil | — | — | — | — | 4 | — | — | — |
| PEG-30 hydrogenated castor oil | — | — | — | — | — | 4 | — | — |
| PEG-40 hydrogenated castor oil | — | — | — | — | — | — | 4 | — |
| PEG-100 hydrogenated castor oil | — | — | — | — | — | — | — | 4 |
| Polyethylene wax | 7 | 7 | 7 | 7 | 7 | 7 | 7 | 7 |
| Coloring material, pearlescent agent | 11 | 11 | 11 | 11 | 11 | 11 | 11 | 11 |
| Evaluation (1): Secondary adhesion resistance effect | A* | A* | A* | A* | C | B | C | C |
| Evaluation (2): Stability of the sample (bulk material) | C | A(X·11) | C | C | C | A | A | A |

※1: Deodorized Polybutene P (manufactured by NIKKO RICA CORPORATION)
※2: Silicone KF54 (viscosity: 400 mm²/s, manufactured by Shin-Etsu Chemical Co., Ltd.)
※3: Methyl phenyl silicone FZ3156 (viscosity: 165 mm²/s. manufactured by Dow Corning Toray Co., Ltd.)
※4: Silicone KF56 (viscosity: 14 mm²/s, manufactured by Shin-Etsu Chemical Co., Ltd.)
※5: ESTEMOL 182V (manufactured by The Nisshin OilliO Group, Ltd.)
※6: WOGEL-18DV (manufactured by MATSUMOTO TRADING Co., Ltd.)
※7: ABIL EM90 (manufactured by Evonik Degussa Japan Co., Ltd,)
※8: Nikkol PMS-SEN (manufactured by Nikko Chemicals Co., Ltd.)
※9: SC0928SL (manufactured by Shin-Etsu Chemical Co., Ltd.)
※10: Nomcort HKG (manufactured by The Nisshin OilliO Group, Ltd.)
※11: The sample was hard.

According to Table 1, the sample of Comparative Example 1, wherein hydrogenated polyisobutene and various methyl phenyl silicones were blended, was excellent in the secondary adhesion resistance effect but the stability was poor.

The samples of Examples 1 to 4, wherein a part of hydrogenated polyisobutene in Comparative Example 1 was substituted by a surfactant such as sorbitan sesquiisostearate, diglyceryl diisostearate, cetyl PEG/PPG-10/1 dimethicone, or propylene glycol monostearate, were excellent in the secondary adhesion resistance effect, and the stability of the bulk material was also excellent.

The sample of Example 5, wherein the blending quantity of each component in Example 1 was varied, was also excellent in the secondary adhesion resistance effect and in stability.

The sample of Example 6, wherein a part of hydrogenated polyisobutene in Example 5 was substituted by mineral oil, was also excellent in the secondary adhesion resistance effect and in stability.

On the other hand, according to Table 2, the samples of Comparative Examples 2 to 9, wherein a part of hydrogenated polyisobutene in Comparative Example 1 was substituted by a surfactant such as lauryl PEG-9 polydimethylsiloxyethyl dimethicone, glyceryl behenate/eicosadioate, sorbitan laurate, sorbitan isostearate, or PEG derivatives of hydrogenated castor oil, were poor in the secondary adhesion resistance effect or in stability.

Subsequently, the present inventors examined the properties of various blended surfactants in Table 1 and Table 2. That is, respective surfactants and hydrogenated polyisobutene or trimethyl pentaphenyl trisiloxane were used in the ratio (surfactant:hydrogenated polyisobutene or trimethyl pentaphenyl trisiloxane=1:1 (mass ratio)) and mixed at 90° C. After the mixture was allowed to stand for 15 minutes, the states of mixture were observed. The evaluation criteria are shown as below. The result is shown in Table 3.
(Evaluation Criteria)
A*: transparent and one phase
A: cloudy and one phase
C: separated

TABLE 3

| | Hydrogenated polyisobutene·※1 | Trimethyl pentaphenyl trisiloxane |
|---|---|---|
| Sorbitan sesquiisostearate·※5 | A* | A* |
| Diglyceryl diisostearate·※6 | A* | A |
| Cetyl PEG/PPG-10/1 dimethicone·※7 | A | A* |
| Propylene glycol monostearate·※8 | A* | A* |
| Lauryl PEG-9 polydimethylsiloxyethyl dimethicone·※9 | C | C |
| Sorbitan isostearate | C | C |
| PEG-10 dimethicone | C | C |
| PEG-10 hydrogenated castor oil | C | A* |
| PEG-30 hydrogenated castor oil | C | A* |
| PEG-40 hydrogenated castor oil | C | C |
| PEG-100 hydrogenated castor oil | C | A* |

According to Table 3, the lipophilic surfactants used in Table 1 and blended in the lip cosmetic excellent in the secondary adhesion resistance effect and in the bulk material stability did not separate when mixed with hydrogenated polyisobutene and methyl phenyl silicone at a high temperature, and they were highly compatible surfactants. On the other hand, the lipophilic surfactants used in Table 2 separated when mixed with hydrogenated polyisobutene and/or methyl phenyl silicone at a high temperature.

Accordingly, in the lip cosmetic of the present invention containing (a) hydrogenated polyisobutene, (b) methyl phenyl silicone(s), and (d) wax, it is necessary to satisfy the conditions that the (c) lipophilic surfactant to be blended does not separate both when mixed with component (a) and when mixed with component (b) at 90° C.

Subsequently, the present inventors studied the blending quantity of (a) hydrogenated polyisobutene. The result is shown in Table 4.

TABLE 4

| | | Comparative Example 10 | Example 7 | Example 1 | Example 8 | Example 9 | Example 10 | Comparative Example 11 |
|---|---|---|---|---|---|---|---|---|
| (a) | Hydrogenated polyisobutene·※1 | 5 | 10 | 15 | 20 | 25 | 30 | 35 |
| (b) | Diphenyl dimethicone·※2 | 24 | 19 | 14 | 9 | 4 | — | — |
| | Trimethyl pentaphenyl trisiloxane·※3 | 40 | 40 | 40 | 40 | 40 | 39 | 34 |
| | Diphenyisiloxy phenyl trimethicone·※4 | 9 | 9 | 9 | 9 | 9 | 9 | 9 |
| (c) | Sorbitan sesquiisostearate·※5 | 4 | 4 | 4 | 4 | 4 | 4 | 4 |
| (d) | Polyethylene wax | 7 | 7 | 7 | 7 | 7 | 7 | 7 |
| | Coloring material, pearlescent agent | 11 | 11 | 11 | 11 | 11 | 11 | 11 |
| Evaluation (1): Secondary adhesion resistance effect | | C | A | A* | A* | A* | A | C |
| Evaluation (2): Stability of the sample (bulk material) | | A | A | A | A | A | A | A |

According to Table 4, in the sample of Comparative Example 10, wherein the blending quantity of hydrogenated polyisobutene was too small, the secondary adhesion resistance effect was poor.

In the sample of Comparative Example 11, wherein the blending quantity of hydrogenated polyisobutene was too large, the secondary adhesion resistance effect was poor.

Accordingly, it is necessary that the blending quantity of (a) hydrogenated polyisobutene blended in the present invention is 10 to 30 mass %.

Subsequently, the present inventors studied the blending quantity of diphenylsiloxy phenyl trimethicone in (b) methyl phenyl silicone. The result is shown in Table 5. In the Table 5 below, the blending quantities are shown in parts by weight.

TABLE 5

| | | Comparative Example 12 | Example 11 | Example 12 | Example 1 | Comparative Example 13 |
|---|---|---|---|---|---|---|
| (a) | Hydrogenated polyisobutene·X·1 | 15 | 15 | 15 | 15 | 15 |
| (b) | Diphenyl dimethicone·X·2 | 14 | 14 | 14 | 14 | 14 |
| | Trimethyl pentaphenyl trisiloxane·X·3 | 40 | 40 | 40 | 40 | 40 |
| | Diphenylsiloxy phenyl trimethicone·X·4 | — | 3 | 6 | 9 | 20 |
| (c) | Sorbitan sesquiisostearate·X·5 | 4 | 4 | 4 | 4 | 4 |
| (d) | Polyethylene wax | 7 | 7 | 7 | 7 | 7 |
| | Coloring material, pearlescent agent | 11 | 11 | 11 | 11 | 11 |
| | Total | 91 | 94 | 97 | 100 | 111 |
| | Evaluation (1): Secondary adhesion resistance effect | A* | A* | A* | A* | C |
| | Evaluation (2): Stability of the sample (bulk material) | C | B | B | A | A |

According to Table 5, in Comparative Example 12, wherein diphenylsiloxy phenyl trimethicone was not blended, the secondary adhesion resistance effect was excellent but the stability of the bulk material was poor.

With an increase in the blending quantity of diphenylsiloxy phenyl trimethicone, the stability of the sample improved (Examples 11, 12, and 1). However, in Comparative Example 13, wherein the blending quantity of diphenylsiloxy phenyl trimethicone was large, the secondary adhesion resistance effect was poor though the stability was excellent.

Accordingly, it is preferable that diphenylsiloxy phenyl trimethicone is blended as component (b) of the lip cosmetic of the present invention and its blending quantity is 1 to 17 mass % relative to the total amount of cosmetic.

Subsequently, the present inventors studied the other components blended in the sample, wherein diphenylsiloxy phenyl trimethicone is not blended in the component (b). The result is shown in Table 6.

TABLE 6

| | | Comparative Example 14 | Example 13 | Example 14 | Example 15 | Example 16 |
|---|---|---|---|---|---|---|
| (a) | Hydrogenated polyisobutene·X·1 | 15 | 15 | 10 | 10 | 10 |
| (b) | Diphenyl dimethicone·X·2 | 39 | 19 | 26 | 18 | — |
| | Trimethyl pentaphenyl trisiloxane·X·3 | 30 | 30 | 26 | 34 | 52 |
| | Diphenylsiloxy phenyl trimethicone·X·4 | — | — | — | — | — |
| (c) | Diglyceryl diisostearate·X·6 | 4 | 4 | 4 | 4 | 4 |
| (d) | Polyethylene wax - microcrystalline wax·X·12 | 7 | 7 | 9 | 9 | 9 |
| | Coloring material, pearlescent agent | 6 | 6 | 5 | 5 | 5 |
| | Decamethylcyclopentasiloxane | — | 13 | 12 | 12 | 12 |
| | Ion-exchanged water | — | 2 | 4 | 4 | 4 |
| | Glycerin | — | 5 | 4 | 4 | 4 |
| | Evaluation (1): Secondary adhesion resistance effect | — | A* | A* | A* | A* |
| | Evaluation (2): Stability of the sample (bulk material) | C | A | A | A | A |
| | Evaluation (3): Stability of the sample (after molding) | C | A | A | A | A |

※12: PA Wax (Manufactured by NIKKO RICA CORPORATION)

According to Table 6, the stability was very poor in Comparative Example 14, wherein diphenylsiloxy phenyl trimethicone was not blended in the component (b) as was the case in Comparative Example 12.

However, the sample of Example 13, wherein a volatile oil component, water, and glycerin were blended in place of component (b) of Comparative Example 14, was excellent in the secondary adhesion resistance effect, and not only the bulk material stability but also the stability after molding were excellent.

The samples of Examples 14 to 16, wherein the blending quantity of hydrogenated polyisobutene was decreased and the blending quantity of component (b) was suitably varied, were also excellent in the secondary adhesion resistance effect and they were also stable.

Accordingly, it was clarified that the stability could be improved by blending a volatile oil component, water, and glycerin even when diphenylsiloxy phenyl trimethicone was not contained in (b) methyl phenyl silicone, which is to be blended in the present invention.

Subsequently, the present inventors studied the preferable blending quantity of water and/or glycerin in the case of blending water and/or glycerin. The result is shown in Table 7.

TABLE 7

|     |                                              | Example 14 | Example 17 | Example 18 | Comparative Example 15 | Comparative Example 16 |
|-----|----------------------------------------------|------------|------------|------------|------------------------|------------------------|
| (a) | Hydrogenated polyisobutene※1                 | 10         | 10         | 10         | 10                     | 10                     |
| (b) | Diphenyl dimethicone※2                       | 26         | 27         | 28         | 29                     | 30                     |
|     | Trimethyl pentaphenyl trisiloxane※3          | 26         | 27         | 28         | 29                     | 30                     |
| (c) | Diglyceryl diisostearate※6                   | 4          | 4          | 4          | 4                      | 4                      |
| (d) | Polyethylene wax - microcrystalline wax※12   | 9          | 9          | 9          | 9                      | 9                      |
|     | Coloring material, pearlescent agent         | 5          | 5          | 5          | 5                      | 5                      |
|     | Decamethylcyclopentasiloxane                 | 12         | 12         | 12         | 12                     | 12                     |
|     | Ion-exchanged water                          | 4          | 3          | 2          | 1                      | —                      |
|     | Glycerin                                     | 4          | 3          | 2          | 1                      | —                      |
| Evaluation (1): Secondary adhesion resistance effect |    | A*         | A*         | A*         | —                      | —                      |
| Evaluation (3): Stability of the sample (after molding) |  | A        | B*         | B*         | C                      | C                      |

According to Table 7, in Example 14, wherein the blending quantities of water and glycerin were large, both the secondary adhesion resistance effect and stability was excellent.

However, when the blending quantities of water and glycerin were decreased, the stability was affected. In Comparative Examples 15 and 16, wherein the sum of the blending quantities of water and glycerin was 2 mass % or less, the stability was poor.

Accordingly, it is preferable that the blending quantities of water and glycerin blended in the lip cosmetic of the present invention are 3 to 12 mass %.

Subsequently, the present inventors studied the percentage of water and/or glycerin blended in the present invention. The result is shown in Table 8.

TABLE 8

|     |                                              | Example 19 | Example 20 | Example 14 | Example 21 | Example 22 |
|-----|----------------------------------------------|------------|------------|------------|------------|------------|
| (a) | Hydrogenated polyisobutene※1                 | 10         | 10         | 10         | 10         | 10         |
| (b) | Diphenyl dimethicone※2                       | 26         | 26         | 26         | 26         | 26         |
|     | Trimethyl pentaphenyl trisiloxane※3          | 26         | 26         | 26         | 26         | 26         |
| (c) | Diglyceryl diisostearate※6                   | 4          | 4          | 4          | 4          | 4          |
| (d) | Polyethylene wax - microcrystalline wax※12   | 9          | 9          | 9          | 9          | 9          |
|     | Coloring material, pearlescent agent         | 5          | 5          | 5          | 5          | 5          |
|     | Decamethylcyclopentasiloxane                 | 12         | 12         | 12         | 12         | 12         |
|     | Ion-exchanged water                          | 8          | 6          | 4          | 2          | —          |
|     | Glycerin                                     | —          | 2          | 4          | 6          | 8          |
| Evaluation (1): Secondary adhesion resistance effect |    | A*    | A*         | A*         | S          | S          |
| Evaluation (3): Stability of the sample (after molding) |  | A     | A          | A          | A          | B*         |

According to Table 8, the samples excellent in the secondary adhesion resistance effect were obtained by increasing the percentage of glycerin. However, it was clarified that the stability became poor when water was not blended.

Accordingly, in the case that water and/or glycerin is blended in the present invention, the percentage of glycerin is preferably 25 to 100 mass % and particularly preferably 25 to 75 mass %.

Subsequently, the present inventors studied the kinds of coloring material blended in the present invention. The result is shown in Table 9.

during application. Therefore, by using a silicone-treated pearlescent agent, a uniform lip cosmetic that is easily dispersible during production can be obtained without affecting the good secondary adhesion resistance at the time of use.

In the following, Lipstick 1 of Example 2 described in the above Table 1 and Lipstick 2, wherein a volatile oil component of the below formulation was blended and that has a secondary adhesion resistance effect, were applied on the

TABLE 9

| | | Test Example 1 | Test Example 2 | Test Example 3 | Test Example 4 | Test Example 5 | Test Example 6 | Test Example 7 |
|---|---|---|---|---|---|---|---|---|
| (a) | Hydrogenated polyisobutene | 15 | 15 | 15 | 15 | 15 | 15 | 15 |
| (b) | Diphenyl dimethicone | 18.5 | 18.5 | 22.5 | 14.5 | 14.5 | 20.5 | 20.5 |
| | Trimethyl pentaphenyl trisiloxane | 35 | 35 | 35 | 35 | 35 | 35 | 35 |
| | Diphenylsiloxy phenyl trimethicone·X·4 | 9 | 9 | 9 | 9 | 9 | 9 | 9 |
| (c) | Sorbitan sesquiisostearate | 2.5 | 2.5 | 2.5 | 2.5 | 2.5 | 2.5 | 2.5 |
| | Diglyceryl diisostearate | 2 | 2 | 2 | 2 | 2 | 2 | 2 |
| (d) | Polyethylene wax | 7 | 7 | 7 | 7 | 7 | 7 | 7 |
| | Coloring material | 9 | 9 | 5 | 13 | 9 | 5 | 5 |
| | Titanated mica | 2 | — | — | — | — | — | — |
| | Dimethicone-treated titanated mica | — | 2 | 2 | 2 | 6 | — | — |
| | Red iron oxide coated titanated mica | — | — | — | — | — | 4 | — |
| | Dimethicone-treated red iron oxide coated titanated mica | — | — | — | — | — | — | 4 |
| Evaluation (1): Secondary adhesion resistance effect | | A* | A* | A* | A* | A* | A* | A* |
| Evaluation (4): Appearance of the sample (bulk material) | | B* | A | A | A | A | B* | A |
| Evaluation (5): Spreadability | | A | A* | S | A | B | A | A* |

The sample of Test Example 1, wherein components (a) to (d) were suitably blended and a pigment and a pearlescent agent (titanated mica) were used as the coloring material, was excellent in the secondary adhesion resistance effect; however, some aggregation of the coloring material was observed.

The sample of Test Example 2, wherein the pearlescent agent in Test Example 1 was substituted by a silicone-treated pearlescent agent, was not only excellent in the secondary adhesion resistance effect but also excellent in the appearance and spreadability.

These trends were the same when red iron oxide-coated titanated mica was used, as the pearlescent agent, instead of titanated mica (Test Example 6 and Test Example 7).

From Test Examples 2 to 5, it was found that the spreadability varied depending on the kind of the coloring material and its blending quantity.

From the above, in the case that a pearlescent agent is blended as the coloring material of the lip cosmetic of the present invention, it is preferable that a silicone-treated pearlescent agent is used. And its blending quantity is preferably less than 5 mass % in view of spreadability.

Since a silicone-treated pearlescent agent normally moves into (b) methyl phenyl silicone during production, it may be considered better not to blend in the system of the present invention in view of the secondary adhesion resistance effect.

However, when a pearlescent agent having a high aspect ratio is applied on the lip, the pearlescent agent normally moves into (a) hydrogenated polyisobutene upon contact five times, respectively. Immediately after the application, a cup was pressed and a picture of the cup was taken and shown in FIG. 1.

According to FIG. 1, it was found that the Lipstick 1 of the present invention had an excellent secondary adhesion resistance effect from immediately after the application.

Formulation (Lipstick 2)
(Silicone Oils)

| | |
|---|---|
| (Perfruoro octyl ethyl/diphenyl dimethicone) copolymer | 23 mass % |
| Trimethyl pentaphenyl trisiloxane | 3 |
| Stearoxy methyl polysiloxane | 2 |
| PEG-10 dimethicone | 4.5 |
| PEG/PPG-19/19 dimethicone | 3 |
| (Film-forming agent) | |
| (Acrylates/propyl trimethicone metacrylate) copolymer | 27 |

(Volatile Oil)

| | |
|---|---|
| Cyclopentasiloxane | 17.5 |
| (Fixation agent) | |
| Ceresin | 6 |
| Candelilla wax | 3 |
| (Others) | |
| Coloring material, pearlescent agent | 11 |

Hereinafter, Formulation Examples and other Comparative Examples of the lip cosmetic of the present invention will be illustrated. It is to be understood that the present invention is not limited by these Formulation Examples and is specified by the scope of claims.

In addition, all the (b) methyl phenyl silicones used in the below-described Formulation Examples 1 to 14 were separated when mixed with (a) hydrogenated polyisobutene at 25° C.

TABLE 10

|   |   | Formulation Example 1 | Formulation Example 2 | Formulation Example 3 | Formulation Example 4 | Comparative Example 17 |
|---|---|---|---|---|---|---|
| (a) | Hydrogenated polyisobutene※1 | 15 | 15 | 15 | 15 | 15 |
| (b) | Diphenyl dimethicone※2 | 12 | 17 | 14 | 11 | — |
|   | Trimethyl pentaphenyl trisiloxane※3 | 30 | 30 | 30 | 30 | 30 |
|   | Diphenylsiloxy phenyl trimethicone※4 | — | 3 | 6 | 9 | 20 |
| (c) | Diglyceryl diisostearate※6 | 4 | 4 | 4 | 4 | 4 |
| (d) | Polyethylene wax - microcrystalline wax※12 | 7 | 7 | 7 | 7 | 7 |
|   | Coloring material | 6 | 6 | 6 | 6 | 6 |
|   | Decamethylcyclopentasiloxane | 12.98 | 4.98 | 4.98 | 4.98 | 4.98 |
|   | Ion-exchanged water | 2 | 2 | 2 | 2 | 2 |
|   | Glycerin | 5 | 5 | 5 | 5 | 5 |
|   | Dipropylene glycol | 1 | 1 | 1 | 1 | 1 |
|   | (Alkyl acrylate/dimethicone) copolymer※13 | 5 | 5 | 5 | 5 | 5 |
|   | Antiforming agent | 0.02 | 0.02 | 0.02 | 0.02 | 0.02 |
| Evaluation (1): Secondary adhesion resistance effect | | A* | A* | A* | A* | C |
| Evaluation (3): Stability of the sample (after molding) | | A | A | A | A | A |

※12: Silicone KP545 (Manufactured by Shin-Etsu Chemical Co., Ltd.)

The components (b) of the comparative example 17 didn't separate when mixed with (a) at 25° C.

TABLE 11

|   |   | Formulation Example 5 | Formulation Example 6 | Formulation Example 7 |
|---|---|---|---|---|
| (a) | Hydrogenated polyisobutene※1 | 10 | 15 | 20 |
| (b) | Diphenyl dimethicone※2 | 38 | 33 | 28 |
|   | Trimethyl pentaphenyl trisiloxane※3 | 20 | 20 | 20 |
| (c) | Diglyceryl diisostearate※6 | 4 | 4 | 4 |
| (d) | Polyethylene wax - microcrystalline wax※12 | 7 | 7 | 7 |
|   | Coloring material | 5 | 5 | 5 |
|   | Decamethylcyclopentasiloxane | 12 | 12 | 12 |
|   | Glycerin | 4 | 4 | 4 |
| Evaluation (1): Secondary adhesion resistance effect | | A* | A* | A* |

In Formulation Example 5, wherein the blending quantity of hydrogenated polyisobutene was 10 mass %, the spreadability and stability were excellent. In Formulation Example 7, wherein the blending quantity of hydrogenated polyisobutene was 20 mass %, the color output was excellent.

TABLE 12

|   |   | Comparative Example 18 | Comparative Example 19 | Comparative Example 20 | Formulation Example 8 | Formulation Example 9 |
|---|---|---|---|---|---|---|
| (a) | Hydrogenated polyisobutene※1 | 20 | 20 | 10 | 10 | 10 |
|   | Diphenyl dimethicone※2 | 27 | 36 | 26 | 34 | 38 |
| (b) | Diphenylsiloxy phenyl trimethicone※4 | 27 | 18 | 26 | 18 | 14 |
| (c) | Diglyceryl diisostearate※6 | — | — | 4 | 4 | 4 |
| (d) | Polyethyiene wax - microcrystalline wax※12 | 9 | 9 | 9 | 9 | 9 |
|   | Coloring material | 5 | 5 | 5 | 5 | 5 |
|   | Decamethylcyclopentasiloxane | 12 | 12 | 12 | 12 | 12 |
|   | Ion-exchanged water | — | — | 4 | 4 | 4 |
|   | Glycerin | — | — | 4 | 4 | 4 |
| Evaluation (1): Secondary adhesion resistance effect | | — | — | C | A* | A* |

The components (b) of the Comparative Example 20 didn't separate when mixed with (a) at 25° C.

TABLE 13

|  |  | Formulation Example 10 | Formulation Example 11 | Formulation Example 12 |
|---|---|---|---|---|
| (a) | Hydrogenated polyisobutene·※1 | 12 | 11 | 10 |
| (b) | Diphenyl dimethicone·※2 | 28 | 28 | 28 |
|  | Trimethyl pentaphenyl trisiloxane·※3 | 28 | 28 | 28 |
| (c) | Diglyceryl diisostearate·※6 | 2 | 3 | 4 |
| (d) | Polyethylene wax - microcrystalline wax·※12 | 9 | 9 | 9 |
|  | Coloring material | 5 | 5 | 5 |
|  | Decamethylcyclopentasiloxane | 12 | 12 | 12 |
|  | Ion-exchanged water | 2 | 2 | 2 |
|  | Glycerin | 2 | 2 | 2 |
|  | Evaluation (1): Secondary adhesion resistance effect | A* | A* | A* |

In Formulation Example 12, wherein the blending quantity of (c) diglyceryl diisostearate was more than 4 mass %, the stability was especially good.

Formulation Example 13

Solid Lipstick

| | |
|---|---|
| Hydrogenated polyisobutene (average molecular weight: 1000) | 15 mass % |
| Trimethyl pentaphenyl trisiloxane | 40 |
| Diphenyl dimethicone | 23 |
| Diphenylsiloxy phenyl trimethicone | 9 |
| Sorbitan sesquiisostearate | 4 |
| Red-colored iron oxide | 1 |
| Lithol Rubin BCA (BaSO₄) | 1 |
| Polyethylene wax | 6 |
| Microcrystalline wax | 1 |

(Production Method)

After heating and solving, the solid lipstick was prepared by stirring and dispersing.

Formulation Example 14

Solid Lipstick

| | |
|---|---|
| Hydrogenated polyisobutene (average molecular weight: 1000) | 15 mass % |
| Trimethyl pentaphenyl trisiloxane | 54 |
| Sorbitan sesquiisostearate | 4 |
| Diphenylsiloxy phenyl trimethicone | 9 |
| Polyethylene wax | 7 |
| Coloring material, pearlescent agent | 11 |

(Production method)

After heating and solving, the solid lipstick was prepared by stirring and dispersing.

DESCRIPTION OF THE NUMERALS

1: A lipstick of Example 2
2: A lipstick of Formulation (Lipstick 2)

The invention claimed is:
1. A lip cosmetic comprising:
(a) 10 to 30 mass % of hydrogenated polyisobutene;
(b) 30 to 70 mass % one or more kinds of methyl phenyl silicones that separate when mixed with (a) at 25° C. wherein the methyl phenyl silicone(s) comprises trimethyl pentaphenyl trisiloxane and optionally one or more selected from the group consisting of diphenylsiloxy phenyl trimethicone and diphenyl dimethicone;
(c) 0.5 to 8 mass % of one or two kinds of lipophilic surfactants that does not separate both when mixed with component (a) and when mixed with component (b) at 90° C. wherein the lipophilic surfactant(s) is selected from the group consisting of sorbitan sesquiisostearate and propylene glycol monostearate;
(d) 5 to 12 mass % of a wax; and
5 mass % or less of a silicone-treated pearlescent agent as a coloring material.
2. The lip cosmetic according to claim 1, wherein a blending ratio (mass ratio) of component (a) and component (b) is component (b)/component (a)=1.1 to 6.
3. The lip cosmetic according to claim 1, wherein component (b) contains diphenylsiloxy phenyl trimethicone.
4. The lip cosmetic according to claim 3, wherein a blending quantity of diphenylsiloxy phenyl trimethicone is 1 to 17 mass % relative to the total amount of the cosmetic.
5. The lip cosmetic according to claim 1, wherein a volatile silicone oil and one or two selected from the group consisting of water and glycerin are contained.
6. The lip cosmetic according to claim 3, wherein a volatile oil component is not contained in the lip cosmetic.
7. A lip cosmetic comprising the following components and none of volatile oil components:
(a) 10 to 30 mass % of hydrogenated polyisobutene;
(b) 30 to 70 mass % of at least two kinds of methyl phenyl silicones that separate when mixed with (a) at 25° C. wherein the methyl phenyl silicones comprise trimethyl pentaphenyl trisiloxane and diphenylsiloxy phenyl trimethicone, and optionally diphenyl dimethicone, wherein said two kinds of methyl phenyl silicones include the diphenylsiloxy phenyl trimethicone at 1 to 17 mass % relative to the total amount of the cosmetic;
(c) 0.5 to 8 mass % of one or two kinds of lipophilic surfactants that does not separate both when mixed with component (a) and when mixed with component (b) at 90° C. wherein the lipophilic surfactant(s) is selected from the group consisting of sorbitan sesquiisostearate and propylene glycol monostearate;
(d) 5 to 12 mass % of a wax; and
5 mass % or less of a silicone-treated pearlescent agent as a coloring material.
8. The lip cosmetic according to claim 2, wherein component (b) contains diphenylsiloxy phenyl trimethicone.
9. The lip cosmetic according to claim 2, wherein a volatile silicone oil and one or two selected from the group consisting of water and glycerin are contained.

10. The lip cosmetic according to claim 3, wherein a volatile silicone oil and one or two selected from the group consisting of water and glycerin are contained.

11. The lip cosmetic according to claim 4, wherein a volatile silicone oil and one or two selected from the group consisting of water and glycerin are contained.

12. The lip cosmetic according to claim 1, wherein a volatile oil component is not contained in the lip cosmetic.

13. The lip cosmetic according to claim 1, wherein the lip cosmetic comprises 2 to 5 mass % of the silicone-treated pearlescent agent.

14. The lip cosmetic according to claim 7, wherein the lip cosmetic comprises 2 to 5 mass % of the silicone-treated pearlescent agent.

* * * * *